(12) United States Patent
Denes et al.

(10) Patent No.: US 7,276,283 B2
(45) Date of Patent: Oct. 2, 2007

(54) PLASMA-ENHANCED FUNCTIONALIZATION OF CARBON-CONTAINING SUBSTRATES

(75) Inventors: Ferencz S. Denes, Madison, WI (US); Sorin Odisei Manolache, Madison, WI (US); Luis Emilio Cruz-Barba, Madison, WI (US); Max G. Lagally, Madison, WI (US); Bradley James Larson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 181 days.

(21) Appl. No.: 10/807,914

(22) Filed: Mar. 24, 2004

(65) Prior Publication Data

US 2005/0214535 A1    Sep. 29, 2005

(51) Int. Cl.
B32B 5/16     (2006.01)
C12N 11/14    (2006.01)

(52) U.S. Cl. ............... 428/403; 435/174; 435/176; 977/847; 977/890

(58) Field of Classification Search ............... 424/490; 435/174, 176; 428/403; 977/847, 890
See application file for complete search history.

(56) References Cited

U.S. PATENT DOCUMENTS

| | | | | |
|---|---|---|---|---|
| 4,568,706 A | * | 2/1986 | Noetzel et al. | 521/149 |
| 4,737,544 A | * | 4/1988 | McCain et al. | 424/443 |
| 5,071,909 A | * | 12/1991 | Pappin et al. | 525/54.1 |
| 5,079,156 A | * | 1/1992 | Mauz et al. | 435/181 |
| 5,080,924 A | | 1/1992 | Kamel et al. | |
| 5,132,108 A | | 7/1992 | Narayanan et al. | |
| 5,306,768 A | | 4/1994 | Hsu et al. | |
| 5,308,641 A | * | 5/1994 | Cahalan et al. | 427/2.1 |
| 5,316,784 A | * | 5/1994 | Maurer et al. | 427/2.13 |
| 5,336,518 A | | 8/1994 | Narayanan et al. | |
| 5,438,077 A | * | 8/1995 | Komiya et al. | 521/37 |
| 5,853,744 A | * | 12/1998 | Mooradian et al. | 424/422 |
| 5,880,552 A | * | 3/1999 | McGill et al. | 310/313 R |
| 5,897,955 A | * | 4/1999 | Drumheller | 428/422 |
| 6,022,902 A | | 2/2000 | Koontz | |
| 6,133,436 A | * | 10/2000 | Koster et al. | 536/24.3 |
| 6,143,354 A | * | 11/2000 | Koulik et al. | 427/2.24 |

(Continued)

FOREIGN PATENT DOCUMENTS

EP    0874242 A1    10/1998

OTHER PUBLICATIONS

Rasmussen, et al., "Covalent Immobilization of DNA into Polystyrene Microwells: The Molecules are only Bound at the 5' End," *Analytical Biochemistry*, 198, pp. 138-142, 1991. Published by Academic Press, Inc. 21.

(Continued)

*Primary Examiner*—H. T Le
(74) *Attorney, Agent, or Firm*—Foley & Lardner LLP

(57) ABSTRACT

Methods for producing plasma-treated, functionalized carbon-containing surfaces are provided. The methods include the steps of subjecting a carbon-containing substrate to a plasma to create surface active sites on the surface of the substrate and reacting the surface active sites with stable spacer molecules in the absence of plasma. Biomolecules may be immobilized on the resulting functionalized surfaces. The methods may be used to treat a variety of carbon-containing substrates, including polymeric surfaces, diamond-like carbon films and carbon nanotubes and nanoparticles.

14 Claims, 6 Drawing Sheets

U.S. PATENT DOCUMENTS

| | | | |
|---|---|---|---|
| 6,159,531 | A | 12/2000 | Dang et al. |
| 6,306,506 | B1 | 10/2001 | Timmons et al. |
| 6,332,363 | B1 * | 12/2001 | Molloy et al. ............... 73/776 |
| 6,402,899 | B1 | 6/2002 | Denes et al. |
| 6,528,020 | B1 * | 3/2003 | Dai et al. .................... 422/98 |
| 6,528,264 | B1 | 3/2003 | Pal et al. |
| 6,602,692 | B1 | 8/2003 | Glusenkamp et al. |
| 6,630,358 | B1 | 10/2003 | Wagner et al. |
| 2003/0163198 | A1 | 8/2003 | Morra et al. |

OTHER PUBLICATIONS

Timofeev, et al., "Regioselective Immobilization of Short Oligonucleotides to Acryl Copolymer Gels," *Nucleic Acids Research*, 24, No. 16, pp. 3142-3148, 1996. Published by Oxford University Press.

Proudnikov, et al., "Chemical Methods of DNA and RNA Fluorescent Labeling," *Nucleic Acids Research*, 24, No. 22, pp. 4535-4532, 1996, Published by Oxford University Press.

Parinov, et al., DNA Sequencing by Hybridization to Microchip Octa- and Decanucleotides Extended by Stacked Pentanucleotides, *Nucleic Acids Research*, 24, No. 15, pp. 2998-3004, 1996. Published by Oxford University Press.

Guschin, et al., Manual Manufacturing of Oligonucleotide, DNA and Protein Microchips, *Analytical Biochemistry*, 250, pp. 203-211, 1997. Published by Academic Press.

Fotin, et al., "Parallel Thermodynamic Analysis of Duplexes on Oligodeoxyribonucleotide Microchips," *Nucleic Acids Research*, 26, No. 6, pp. 1515-1521, 1998. Published by Oxford University Press.

Proudnikov, et al., Immobilization of DNA in Polyacrylamide Gel for the Manufacture of DNA and DNA-Oligonucleotide Microchips, *Analytical Biochemistry*, 259, pp. 34-41, 1998. Published by Academic Press.

Wang, et al., "Polishable and Renewable DNA Hybridization Biosensors," *Anal Chem*, 70, pp. 3699-3702, 1998. Published by the American Chemical Society.

Alvarez-Blanco, et al., "A Novel Plasma-enhanced Way for Surface-functionalization of Polymeric Substrates," *Polymer Bulletin*, 47, pp. 329-336, 2001. Published by Sprinter-Verlag.

Ivanova, et al., Feasibility of Using Carboxylic-rich Polymeric Surfaces for the Covalent Binding of Oligonucleotides for microPCR Applications, *Smart Mater. Struct.*, 11, pp. 783-791, 2002. Published by Institute of Physics Publishing.

Metzger, et al., Signal to Noise Comparison Accelr8 OptArray vs. The Leading Polymer and Silane Microarray Slide Chemistries, *Technical Bulletin*, No. TB0400, 2002.

Yang, et al., "DNA-modified Nanocrystalline Diamond Thin-films as Stable, Biologically Active Substrates," *Nature Materials*, 1, No. 4, pp. 253-257, 2002. Published by Nature Publishing Group.

Liu, et al., "DNA Probe Attachment on Plastic Surfaces and Microfluidic Hybridization Array Channel Devices with Sample Oscillation," *Analytical Biochemistry* 317, pp. 76-84, 2003. Published by Academic Press.

http://www.surmoodics.com/pageDetail.aspx?pageId=10 &menuID=10—"Biomolecule Immobilization", website article printed on Feb. 19, 2004.

http://www.surmodics.com/pageDetail.aspx?pageId=7 &menuID=7—"Photolink Manufacturing Process", website article printed on Feb. 19, 2004.

http.//www/vwrcanlab.com- "A Specific Surface for a Specific Application." Website.

Podyminogin, et al., "Attachment of Benzaldehyde-modified Oligodeoxynucleotide Probes to Semicarbazide-Coated Glass," *Nucleic Acids Research*, vol. 29, No. 24, pp. 5090-5098, 2001. Published by Oxford University Press.

Cheung, et al., "5'-Thiolated Oligonucleotides on (3-Mercaptopropyl) trimethoxysilaten-Mica: Surface Topography and Coverage," printed from Web, Jun. 5, 2003. Published by American Chemical Society.

"Motorola Goes for Organic Growth with Biochips," http://www.groupweb.com/sci_tech/jun_30/motorola.html Website article printed on Jan. 2, 2000.

"Motorola's Biochip Center Aims for a Healthier World," http://www.edtn.com/story/tech/OEG19990216S0030-R. Website article printed on Aug. 6, 2004.

"EasySpot Microarray Slide," http://www.u-vision-biotech.com/english/product_service/easy_oligo. Website article printed on Feb. 19, 2004.

"Novel surface chemistry for DNA immobilization," http://hamers.chem.wisc.edu/research/bioattachment/dna_on_silicon.htm. Website article printed on Mar. 2, 2003.

"Motorola and Packard to produce 'biochips'" http://www4.nando.net/newsroom/ntn/health/062998/health7_12937_noframes.html. Website article printed on Jan. 2, 2000.

http://www.whatis.com/biochip.html. Website article printed on Jan. 2, 2000.

"New "Biochips" Aimed at Medicine, Agriculture," http://www.pcworld.com/pcwtoday/article/0,1510,7313,00.html. Website article printed on Jan. 2, 2000.

http://arrayit.com/Products/Substrates/. Website article printed on Aug. 9, 2004.

http://arrayit.com/Products/Substrates/SME/sme.html. Website article printed on Aug. 6, 2004.

\* cited by examiner

PLASMA-ENHANCED FUNCTIONALIZATION OF CARBON-CONTAINING SUBSTRATES

STATEMENT OF GOVERNMENT RIGHTS

Research finding was provided for this invention by the USDA Cooperative State Research, Education, and Extension Service (CSREES) under Grant Number 2001-35103-10109. The federal government has certain rights in this invention.

FIELD OF THE INVENTION

This invention pertains generally to the plasma treatment and functionalization of carbon-containing surfaces.

BACKGROUND OF THE INVENTION

Bioactive surfaces made from surface-bound biomolecules may be used in a variety of bioassays, biosensors and other devices. For example, polymer-bound oligonucleotides find applications in hybridization-based diagnostics and in the discovery of new therapeutics based on molecular recognition. Prenatal diagnostics of genetic aberrations, identification of virus born diseases, detection of mutations of regulatory proteins controlling carcinogenesis, and novel hybridization-based identification techniques oriented to forensic or archaeology fields are some of the potential applications.

Bioactive surfaces may also play an essential role in areas other than medicine, pharmaceutics and biotechnology. Development of ultra-selective chemical sensors and absorbent surfaces are crucial for creating environmentally safe processes. Monitoring the quality of water is one of the major demands in this area. Biomolecular-based chemical sensors and filters for toxic chemicals and microorganisms (e.g., *E. coli*) will play a significant role in future technologies.

Proteins, and enzymes in particular, are one class of biomolecules commonly used to make bioactive surfaces. The advantages of using enzymes in bioassays and biosensors are related to their very high specificity (regio- and stereo-specificity) and versatility, mild reaction conditions (close to room temperatures and to pH neutral media), and to their high reaction rates. However, due to the poor recovery yields and reusability of free enzymes, much attention has been paid in the last few years to the development of efficient enzyme immobilization processes. Most biologically-active in vivo species, such as enzymes and antibodies, function in heterogeneous media. These environments are difficult to reproduce in vitro for industrial utilization. Immobilized enzyme systems are useful for experimental and theoretical research purposes for understanding the mechanisms of in vivo, bio-catalyzed reactions, and offer solutions for use in batch-type reactions, where there is poor adaptability to various technological designs and recovery of the enzymes is difficult.

The activity of enzymes (polypeptide molecules) are based on their complex three-dimensional structures containing sterically exposed, specific functionalities. The polypeptide chains are folded into one or several discrete units (domains), which represent the basic functional and three-dimensional structural entities. The cores of domains are composed of a combination of motifs which are combinations of secondary structure elements with a specific geometric arrangement. The molecular-structure-driven chain-folding mechanisms generate three-dimensional enzyme structures with protein molecules orienting their hydrophobic side chains toward the interior and exposing a hydrophilic surface. The —C(R)—CO—NH— based main chain is also organized into a secondary structure to neutralize its polar components through hydrogen bonds. These structural characteristics are extremely important and they make the enzyme molecules very sensitive to the morphological and functional characteristics of the potential immobilizing substrates. High surface-concentrations of enzyme-anchoring functionalities can result, for instance, in excessive enzyme-densities or multi-point connections which can "neutralize" the active sites or can alter the three-dimensional morphologies of the enzyme molecules through their mutual interaction and their interaction with the substrate surfaces. These are just a few of the factors which may be responsible for the significantly lower activities of immobilized-enzymes in comparison to the activities of free enzyme molecules. Rough substrate surface topographies or stereoregular surfaces (e.g., isotactic or syndiotactic polymers) might also influence, in a positive or negative way, the specific activities. Morphologically ordered surfaces might induce changes of the stereoregular shapes of protein molecules. It has also been found that enzymes can adopt more than one functional conformation other than its lowest potential energy state. E. S. Young, et al., Anal. Chem. Vol. 69, 1977, pp. 4242, et seq.

A number of approaches have been proposed for immobilizing bioactive molecules, such as enzymes on polymeric substrates. Most natural and synthetic polymeric substrates can easily be functionalized through polymer-analog reactions. Main chain and side-group homogeneous reactions are the most common approaches. The use of polymers as "carriers" or "supports" for chemical reagents, catalysts or substrates represents a relatively new, significant, and rapidly developing area. The polymer is in the form of an insoluble, inert substrate that may be a solvent-swollen, crosslinked gel, or a surface active solid. This approach eases the separation of reagents or catalysts (e.g., enzymes) from the reaction products, permitting the automation of the complex chemistry. However, the specific structure of the repeating units of the macromolecules often limit considerably the variety of polymer-analog reactions. These reactions are even more difficult to develop under heterogeneous environments. Natural and even some synthetic polymeric substrates can also undergo undesired chemical modifications, and sometimes biodegradation, during the polymer-supported organic reactions. Moreover, inert polymeric substrates (e.g., polyethylene, polypropylene, polyethylene terephthalate (PET), and polytetrafluoroethylene (PTFE)) and inorganic supports (e.g., glass, silica) cannot be functionalized efficiently by using conventional wet chemistry approaches.

The most widely used synthetic polymer surfaces are usually characterized by low surface energy values, and some of the thermoplastics, including polyethylene and polypropylene, for example, are essentially chemically inert. Modification of characteristics like adhesion, wettability, dyeability, and reactivity for such materials necessitates the creation of particular functionalities on the surfaces of such polymer substrates.

Cold plasma processing has shown promise for the functionalization of organic and inorganic substrates. See, e.g., D. T. Clark, et al., Polymer Surfaces (book), John Wiley & Sons, New York, 1978, pp. 185-210; F. Denes, et al., "Surface Modification of Polysaccharides Under Cold Plasma Conditions," in Polysaccharides. Structural Diversity and Functional Versatility (book), Eds. Dumitriu, Marcel Dekker, Inc., New York, 1998; Plasma Surface Modification of Polymers: Relevance to Adhesion (book), Eds. M. Strobel, et al., VSP, Utrecht, The Netherlands, 1994; F. Denes, TRIP, Vol., No. 1, 1997, pp. 23, et seq. Numerous experiments performed in recent years in plasma laboratories under various internal and external plasma conditions and reactor geometries clearly indicate that inert and reactive-gas discharges are effective for the surface modification (functionalization) of even the most inert materials, such as polypropylene, Teflon®, silica, etc. The industrial applications of macromolecular plasma chemistry are rapidly developing. Large capacity reactors and continuous flow system plasma installations have been designed, developed and tested.

Several polymeric substrates have already successfully been functionalized with biomolecules using plasma techniques. For example, active horseradish peroxidase has been immobilized on acrylic acid and acrylamide radiation-grafted polymer surfaces. See H. Hongfei, et al., Radiat. Phys. Chem., Vol. 31, 1988, pp. 761 and A. A. Alencar, et al., Radiat. Phys. Chem., Vol. 55, 1999, p. 345. In these studies a cold plasma-technique was used for the surface functionalization. Immobilization of bioactive molecules onto synthetic and natural polymeric material surfaces often requires the presence of primary amine functionalities. Early attempts considered for the plasma-enhanced implantation of primary amine functionalities were ammonia discharge environments. However, due to the extensive fragmentation of NH3, other saturated, non-saturated and aromatic amines were also used as primary amine group precursors. Recently it has been shown that hydrazine-RF-plasmas are more adequate in comparison to ammonia discharges for the generation of surface primary amine functionalities on synthetic polymer surfaces. See Denes et al., J. Photopolym. Sci. Technol., Vol. 12, 1999, pp. 27 and Martinez et al., J. Biomater. Sci.: Polym. Ed., Vol. 11, 2000, pp.415.

Non-equilibrium plasma-mediated surface functionalization reactions have their shortcomings, however. Most of the precursor molecules of the desired surface functionalities (e.g., ammonia, hydrazine, saturated and non-saturated amines, etc.) undergo plasma-induced, intense fragmentation processes. As a consequence, undesirable functionalities will be implanted onto the substrate surfaces. These processes are also accompanied by the production of extremely reactive surface-free-radicals, and charged centers, which can induce further active-surface-mediated chemical reactions with the gas-phase plasma components through a variety of pathways. Plasma-generated free radicals (surface and stable, caged free radicals) can also initiate non-specific interactions with target molecules (e.g., biomolecules) under in situ or ex situ environments in the absence of plasma, which significantly diminishes the molecular recognition capabilities of the modified substrates.

SUMMARY OF THE INVENTION

Low- or atmospheric pressure RF-plasma-enhanced surface treatment methods are provided for the surface functionalization of carbon-containing substrates, such as polymeric substrates. The methods take advantage of high reactivity plasma-generated active sites located on carbon-containing substrate surfaces, which can promote under in situ conditions, heterogeneous chemical reactions with stable gas-phase molecules in the absence of plasma.

Carbon-containing surfaces treated using the methods provided herein may be fabricated with a higher density of bound biomolecules than similar surfaces fabricated using wet chemical techniques. The use of a plasma approach makes it possible to fabricate such surfaces with small quantities of starting materials, while avoiding many of the environmentally unfriendly chemicals that are typically employed in wet chemical techniques. This significantly enhances environmental safety while reducing costs. In addition, biosensors and assays made from the surfaces typically experience less non-specific binding than sensors and assays made using conventional wet chemistry approaches. As a result, devices made using the methods provided herein are more reliable and more sensitive that other similar devices presently available.

The methods provided herein are well suited for the production of substrates for molecular recognition and molecular manufacturing applications which require immobilized biomolecules. The enhanced sensitivity of the surfaces provided herein make them well-suited for use in a variety of applications, such as biochips and biosensors, including flexible, thin-film biosensors that can be integrated into traditional microelectronics. Specific examples of applications for which the surfaces may be used include hybridization assays, fluorescence assays and luminescence assays.

In a first step of the methods provided herein, a carbon-containing substrate is exposed to an inert plasma under conditions that promote the generation of reactive active sites, such as free radicals and ions, at the surface of the substrate. In a subsequent step, the active sites on the surface are reacted with molecules of a reactant gas in the absence of plasma to provide surface-bound spacer chains. The surface-bound spacer chains include one or more reactive functional groups and, as such, produce a functionalized substrate surface.

The methods are well adapted to immobilize biomolecules on a variety of carbon-containing substrates. In one variation of the method, the immobilization of biomolecules on a substrate surface is a three-step process. In a first step, the substrate is exposed to a plasma to produce active sites on the surface thereof. Next, the active sites on the substrate undergo in situ gas-phase reactions with spacer molecules in the absence of plasma to provide surface-bound spacer chains on the substrate surface. Finally, biomolecules are immobilized on the surface by reacting them with the spacer chains. In this variation of the method, the spacer molecules are characterized in that they include a first functional group capable of reacting with the substrate surface to form a covalent bond between the spacer molecule and the surface and a second functional group capable of reacting with a biomolecule to form a covalent bond between the spacer molecule and the biomolecule. As such, the spacer molecules serve to anchor the biomolecules to the underlying substrate. Thus, by selecting spacer molecules with an appropriate chain length, the distance between the immobilized biomolecules and the substrate surface may be tailored to fit a selected application.

In another variation of the method, biomolecules may be tethered to the surface through extended spacer chains, which include one or more spacer chain extender molecules, covalently bound to the substrate surface. As with the previous variation of the method, a substrate surface is first exposed to a plasma to produce active sites and the active sites are then reacted with a first reactant gas of spacer molecules in situ in the absence of plasma to provide surface-bound spacer chains on the substrate surface. The surface-bound spacer chains are then reacted with a second reactant gas of spacer chain extender molecules in situ in the absence of plasma to provide an extended spacer chain. The extended spacer chain may be further extended through one or more additional extension reactions by reacting the chains with additional gas-phase spacer chain extender molecules in a series of consecutive gas phase reactions. Finally, biomolecules may be immobilized on the surface by reacting them with the terminal spacer chain extender molecules of spacer chains. In this variation of the method, the spacer molecules are characterized in that they include a first functional group capable of reacting with the substrate surface to form a covalent bond between the spacer molecule and the surface and a second functional group capable of reacting with a spacer chain extender molecule to form a covalent bond between the spacer molecule and the spacer chain extender molecule. Similarly, the spacer chain extender molecules of the second reactant gas each include a first functional group capable of reacting with a spacer molecule to form a covalent bond between the spacer chain extender molecule and the spacer molecule and a second functional group capable of reacting with a biomolecule or another spacer chain extender molecule to form a covalent bond between the spacer chain extender molecule and the biomolecule or between the first spacer chain extender molecule and a second spacer chain extender molecule. As such, the extended spacer chains serve to tether the biomolecules to the underlying substrate. Thus, by selecting the number and length of spacer molecules and spacer chain extender molecules that go into producing the extended spacer chains, the distance between the immobilized biomolecules and the substrate surface may be tailored to fit a selected application.

Thus, from the discussion above, it should be understood that the term "spacer chain" may refer to a single spacer molecule covalently bound between a surface and a biomolecule or a chain made from two of more spacer molecules (i.e., an extended spacer chain) wherein the terminal spacer molecule on one end of the chain is covalently bound to a surface, the terminal spacer molecule on the opposite end of the chain is covalently bound to a biomolecule and any intervening spacer molecules serve to increase the separation between the surface and the biomolecule. As used herein, the term "spacer chain" does not include any molecular chains or functionalities associated with a biomolecule prior to the reaction of that biomolecule with the surface-bound spacer chains.

The methods provided herein may be used to functionalize the surfaces of a broad range of carbon-containing substrates, including polymeric substrates, diamond-like carbon films, and carbon nanoparticles.

Further objects, features and advantages of the invention will be apparent from the following detailed description when taken in conjunction with the accompanying drawings.

DETAILED DESCRIPTION

Figure 1:
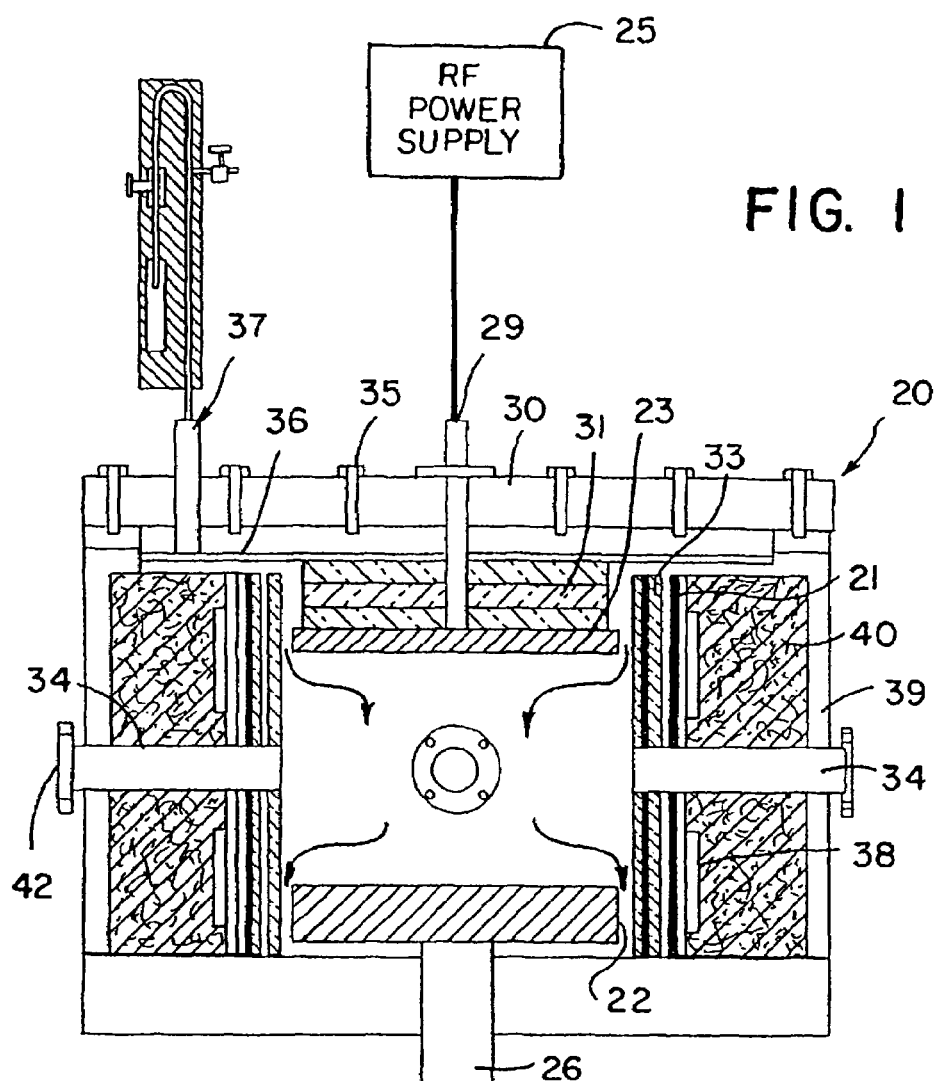
FIG. 1 shows a parallel plate reactor that may be used to carry out a surface plasma treatment in accordance with the present invention.

Plasma-enhanced, in situ surface functionalization processes which take advantage of high reactivity surface-species created by plasma are provided. During the first step of the processes, free radicals and/or charged species are generated under gas discharge (e.g., argon plasma) environments on carbon-containing substrate surfaces. In a second step, the plasma-treated surface is reacted with stable gas molecules in the absence of plasma. Unlike plasma-based surface treatments that functionalize a surface using a plasma of precursor molecules, the present methods avoid the fragmentation of the gas molecules that typically take place in a plasma, minimizing, the production of unwanted surface functionalities. Unlike conventional wet chemical approaches to functionalizing polymeric surfaces, the present methods do not require solvents or catalysts to functionalize the surface. Moreover, compared to wet chemical surface functionalization techniques, the present methods produce surfaces having a higher density of functionalities with much shorter treatment times.

In accordance with the methods provided herein, surface treatment begins by exposing a substrate to a radiofrequency (RF) plasma discharge under conditions that promote the formation of surface active sites, including neutral (e.g., free radical) and/or charged (e.g., ions) active sites. This plasma-treatment step is carried out utilizing cold-plasma processing techniques. Cold plasmas are non-thermal and non-equilibrium plasmas, as compared with hot plasmas which are thermal or equilibrium plasmas. In a cold plasma, the kinetic energy of the electrons is high while the kinetic energy of the atomic and molecular species is low.

The selection of appropriate plasma parameters for the creation of active sites may depend on the specific design of the reactor and on the relative geometric positioning of the target or substrate holding electrode in the reactor chamber. The plasma is generally a low-pressure plasma, although atmospheric pressure plasmas may also be employed. Typical reactor conditions include a gas pressure of no more than about 400 mTorr, desirably no more than about 250 mTorr and a RF-power dissipated to the electrodes of no more than about 250 W, desirably no more than about 200 W. However, as one of skill in the art would recognize, reactor conditions outside these ranges may also be employed. Generally, only a relatively short exposure to the plasma discharge is needed. For example, in some embodiments of the surface treatment methods, the substrate is exposed to the plasma for no more than about 20 minutes. This includes embodiments where the substrate is exposed to the plasma for no more than about 10 minutes and further includes embodiments where the substrate is exposed to the plasma for no more than about 5 minutes.

A variety of gases may be used to produce the plasma discharge, provided the chosen gas is capable of creating active sites on the substrate surface under plasma conditions. Typically, the gas will be an inert gas, such as argon.

However, other gases may be used, including, but not limited to hydrogen, oxygen and argon/hydrogen mixtures.

An example of a preferred parallel plate reactor provided with temperature control capabilities that can be utilized for plasma treatment in accordance with the invention is shown at 20 in FIG. 1. The reactor 20 is provided with heating capabilities (in the range of 25-500° C.) for the reaction chamber. The reactor is composed of a cylindrical stainless steel reaction chamber 21 in which a 20 cm diameter and a 0.8 cm thick lower, grounded electrode 22 and an (identical dimensions) upper, stainless steel electrode 23 are located. The upper electrode 23 is connected to a conventional RF-power supply 25. Conventional power supplies are available at 40 kHz and 13.56 MHz (operable CW or pulsed). Typically, the MHz and kHz power supplies are separate units. Both electrodes are preferably removable, which facilitates post-plasma cleaning operations. The lower electrode 22 is also a part of the vacuum line 26 through supporting conically shaped and circularly-perforated stainless steel tubing. The evacuation of the chamber 21 is performed uniformly through the narrow gap (3 mm) existing between the lower electrode 22 and the bottom of the reaction chamber. The upper electrode 23 is directly connected to the threaded end of a vacuum-tight metal/ceramic feedthrough 29 which assures both the insulation of the RF-power line from the reactor and the dissipation of the RF-power to the electrodes. The space between the upper electrode and the upper wall 30 of the reaction chamber is occupied by three 1 cm thick and 20 cm diameter Pyrex-glass removable disks 31. These discs insulate the electrode from the stainless steel top of the reactor and allow adjustment of the electrode to electrode gap. The reactor volume located outside of the perimeter of the electrodes is occupied by two Pyrex-glass cylinders 33 provided with four symmetrically located through-holes 34 for diagnostic purposes. This reactor configuration substantially eliminates the non-plasma zones of the gas environment and reduces considerably the radial diffusion of the plasma species, leading consequently to a more uniform plasma-exposure of the substrates being treated. As a result, uniform surface treatments can be achieved. The removable top of the reactor allows the reaction chamber to be vacuum sealed with the aid of a copper gasket and fastening bolts 35. This part of the reactor also accommodates a narrow circular gas-mixing chamber 36 provided with a shower-type, 0.5 mm diameter orifices system, and with a gas supply connection 37. This gas supply configuration assures a uniform penetration and flow of the gases and vapors through the reaction zone. The entire reactor chamber can be heated with electric heaters 38 attached to the outside surface of the chamber. The reactor chamber is enclosed in an aluminum-sheet 39 which protects a glass-wool blanket 40 that surrounds the sides of the reactor chamber to reduce thermal energy loss. Four symmetrically positioned stainless steel porthole tubes pass through the insulating blanket and are connected and welded to the reactor wall for diagnostic purposes. These portholes are provided with exchangeable, optically smooth, quartz windows 42.

Figure 2:
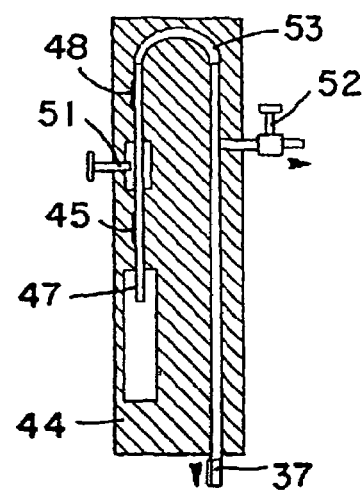
FIG. 2 shows the gas reservoir, valve and connecting tubing of the reactor of FIG. 1.

The gas reservoir, valve and the connecting stainless steel tubing are shown in greater detail in FIG. 2 and, as shown, are embedded in two shape-designed, 1 cm thick copper-jackets 44 provided with controlled electric heaters 45. The vapor supply assemblage is composed of a reservoir 47, VCR connectors 48, needle valves 51 and 52, and connecting tubing 53. The entire system is insulated using a glass-wool blanket coating.

The reactor 20 thus may be utilized to control the temperature of the reactor chamber and the substrate to achieve desired plasma operating conditions. Inductively coupled plasma reactors and other closed reactors may be utilized as well as corona discharge devices, examples of which are discussed below.

Figure 3:
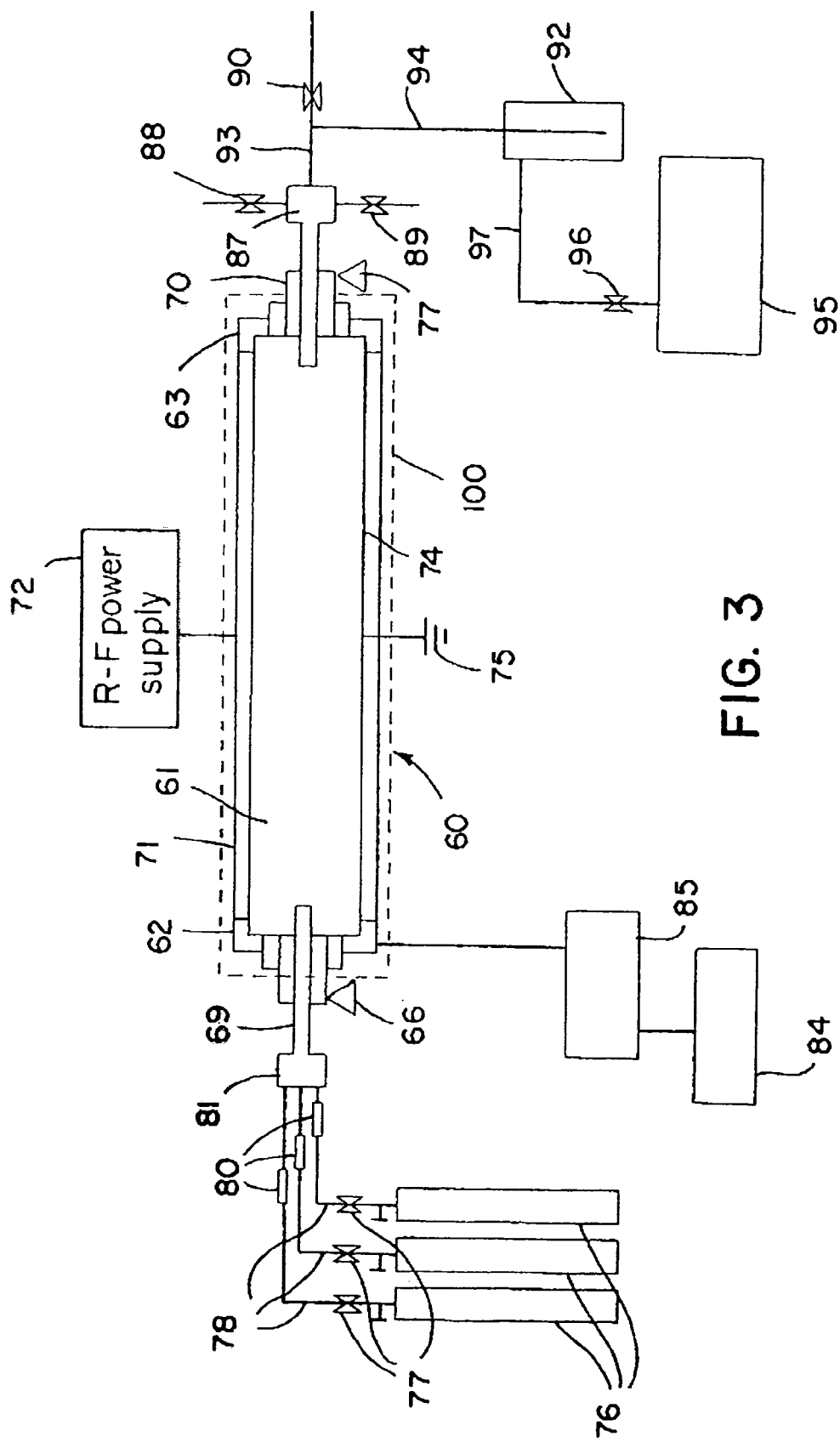
FIG. 3 shows a rotary reactor that may be used to carry out a surface plasma treatment in accordance with the present invention.

An exemplary cold plasma rotary reactor system which may be utilized to carry out the invention is shown in FIG. 3 at 60. Such a rotary system is especially well suited to the plasma treatment of fibers, powders and other particulate matter. The reactor system includes a cylindrical reaction vessel 61 (e.g., formed of Pyrex® glass, 1 m long and 10 cm inside diameter) which is closed at its two ends by disk-shaped stainless steel sealing assemblies 62 and 63. The end assemblies 62 and 63 are mounted to mechanical support bearings 66 and 67 which engage the sealing assemblies 62 and 63 to enable rotation of the reaction vessel 61 about its central axis, i.e., the central axis of the cylindrical reaction vessel. Hollow shaft (e.g., 0.5" inside diameter) ferrofluidic feedthroughs 69 and 70 extend through the sealing assemblies 62 and 63, respectively, to enable introduction of gas into and exit of gas from the reaction chamber. A semi cylindrical, outside located, copper upper electrode 71 is connected to an RF power supply 72, and a lower, similar semi cylindrical copper electrode 74 is connected to ground (illustrated at 75). The two electrodes 71 and 74 closely conform to the cylindrical exterior of the reaction vessel 61 and are spaced slightly therefrom, and together extend over most of the outer periphery of the reaction vessel but are spaced from each other at their edges a sufficient distance to prevent arcing or discharge between the two electrodes.

The source gas is held in containers 76, e.g., storage tanks. The flow of gas from a source cylinder 76 is controlled by needle valves and pressure regulators 77 which may be manually or automatically operated. The gas that passes through the control valves 77 is conveyed along supply lines 78 through flow rate controllers 80 to a gas mixing chamber 81 (e.g., preferably of stainless steel), and an MKS pressure gauge (e.g., Baratron) may be connected to the mixing chamber 81 to monitor the pressure thereof. The mixing chamber 81 is connected to the feedthrough 69 that leads into the interior of the reaction chamber 61. A digital controller 84 controls a driver motor 85 that is connected to the assembly 62 to provide controlled driving of the reaction chamber in rotation.

The second feedthrough 70 is connected to an exhaust chamber 87 to which are connected selectively openable exhaust valves 88, 89 and 90, which may be connected to conduits for exhaust to the atmosphere or to appropriate recovery systems or other disposal routes of the exhaust gases. A liquid nitrogen trap 92 is connected to an exhaust line 93 which extends from the chamber 87 by stainless steel tubing 94. The trap 92 may be formed, e.g., of stainless steel (25 mm inside diameter). A mechanical pump 95 is connected through a large cross-section valve 96 via a tube 97 to the trap 92 to selectively provide vacuum draw on the reactor system to evacuate the interior of the reaction chamber 61 to a selected level.

The power supply 72 is preferably an RF power supply (e.g., 13.56 MHz, 1,000 W) which, when activated, provides RF power between the electrodes 71 and 74 to capacitively couple RF power to the gas in the reaction chamber within the reaction vessel 61. Conventional coils for inductively coupling RF power to the plasma may also be used (e.g., a coil extending around the reaction vessel 61). A Faraday cage 100 is preferably mounted around the exterior of the reaction vessel to provide RF shielding and to prevent accidental physical contact with the electrodes.

The reactor vessel may be rotated by the drive motor 85 at various selected rotational speeds (e.g., 30-200 rpm), and it is preferred that the vacuum pump and associated connections allow the pressure in the reaction chamber within the vessel to be selectively reduced down to 30 mTorr.

The following are examples of commercial parts that may be incorporated in the system 60: RF-power supply 85 (Plasma Therm Inc. RTE 73, Kresson N.J. 08053; AMNS-3000 E; AMNPS-1); mechanical vacuum pump 95 (Leibold-Heraeus/Vacuum Prod. Inc., Model: D30AC, Spectra Vac Inc); pressure gauge (MKS Baratron, Model: 622A01TAE); digitally controlled rotating system 84, 85 (DC motor Model 4Z528, Dayton Electric Mfg. Co.; DART Controls Inc. controller).

In utilization of the plasma treatment system 60 in accordance with the invention, it is generally preferred to carry out a plasma-enhanced cleaning of the reactor prior to treatment to eliminate possible contaminants. An exemplary cleaning step includes introduction of oxygen gas from one of the tanks 76 into the reaction chamber and ignition of a plasma in the gas at, e.g., a power level of 300 W, a gas pressure of 250 mTorr, an oxygen flow rate of 6 sccm, and a typical cleaning period of 15 minutes.

Once the active sites have been generated on the substrate surface by plasma-treatment, they are reacted with a gas containing spacer molecules in the absence of plasma. This may be accomplished by exposing the plasma-treated surface to the gas in situ, that is, without first breaking the vacuum in the plasma reactor chamber or otherwise exposing the surface to the atmosphere. This step occurs without substantial fragmentation of the spacer molecules in the gas. If the active sites on the surface are exposed to atmosphere before being exposed to the spacer molecules, they will react with oxygen and nitrogen in the atmosphere, producing unwanted functional groups on and deactivating the surface. Typically, the plasma reactor chamber is pumped down after the plasma treatment step and, without breaking the vacuum, the gas is introduced into the chamber. The necessary exposure time is typically quite short. In some embodiments, the active sites are exposed to the gas for no more than about 30 minutes. This includes embodiments where the active sites are exposed to the gas for no more than about 20 minutes and further includes embodiments where the active sites are exposed to the gas for no more than about 10 minutes. The spacer molecules should have a reasonably high vapor pressure at room temperature, desirably, but not necessarily, at least about 200 mTorr.

The spacer molecules in the gas are characterized in that they include a first functional group capable of reacting with the carbon-containing substrate surface to form a covalent bond to that surface. Once these spacer molecules are bound to the surface they may serve as anchoring points for biomolecules or spacer chain extender molecules. The spacer molecules are further characterized in that they include a second functional group capable of reacting with a biomolecule or a spacer chain extender molecule. In the former embodiment, the spacer molecule serves as a tether between a biomolecule and an underlying surface. In the latter embodiment, the spacer molecule may be used to tether a biomolecule to a surface though one or more intervening spacer chain extender molecules. The first and second functional groups may be the same or different.

In some embodiments, the spacer molecules are diamine molecules, such as ethylene diamine or hydrazine molecules. In these embodiments the first of the two amine groups on each molecule reacts with an active site on the carbon-containing substrate surface and the second of the two amine groups provides a reactive functionality with which a spacer chain extender molecule may be reacted to provide a spacer chain. Epihalohydrin molecules, particularly epichlorohydrin molecules, are also suitable spacer molecules. Such molecules react with active sites on the surface, presenting an epoxide functionality capable of reacting with an amine-containing biomolecule. Analogs of epichlorohydrin, such as epibromohydrin and epifluorohydrin, may also be employed as spacer molecules. Diepoxide molecules, such as 1,4-butanediol diglycidyl ether, may also be employed.

Once the spacer molecules are bound to the substrate surface, these spacer molecules may be reacted with one or more spacer chain extender molecules in the gas phase, in the absence of plasma, to provide an extended spacer chain for tethering a biomolecule to the surface. Alternatively, the spacer molecules may be reacted directly with biomolecules to immobilize the biomolecules on the surface, as in the case of epichlorohydrin. Where an extended spacer chain is desired, the surface-bound spacer molecules are exposed in situ to a reactant gas containing the spacer chain extender molecules. The necessary exposure time is typically quite short. In some embodiments, the spacer chains are exposed to a gas containing the spacer chain extender molecules for no more than about 30 minutes. This includes embodiments where the spacer chains are exposed to a gas containing the spacer chain extender molecules for no more than about 20 minutes and further includes embodiments where the spacer chains are exposed to a gas containing the spacer chain extender molecules for no more than about 10 minutes. Like the spacer molecules, the spacer chain extender molecules desirably have a reasonably high vapor pressure at room temperature. The spacer molecules and spacer chain extender molecule are typically low molecular weight (e.g., Mw~500 or less) organic molecules containing between 2 and 20 carbon atoms.

The spacer chain extender molecules are characterized by at least two functional groups which may be the same or different. The first functional group of a spacer chain extender molecule is capable of reacting with the second functional group of a surface-bound spacer molecule to form a covalent bond. Together the spacer molecule and its bound spacer chain extender molecule form an extended spacer chain. The second functional group of a spacer chain extender molecule is capable of reacting with either another spacer chain extender molecule, to further extend the length of the chain, or a biomolecule to tether the biomolecule to the surface.

Multiple sequential spacer chain extension steps may be used to tailor the length of the spacer chains. In each of these steps the surface-bound spacer chains undergo in situ vapor-phase reactions with additional spacer chain extender molecules, in the absence of plasma, to become covalently bound to the existing spacer chains. After each step, the non-reacted components are evacuated from the reaction chamber. In this manner, chains of spacer molecules of a desired length can be built up. The terminal spacer molecules in the chain may then be exposed to a biomolecule to which it will bond, thereby providing active biomolecules bound to the substrate surface. In this manner, long spacer chains may be built up in a step-wise fashion to produce spacer chains longer than those provided using wet chemical methods. For example, in some embodiments the spacers chains may be at least 2.5 nm in length, where the length of the chain is calculated from the bond lengths between the atoms making up the chain. This includes embodiments where the spacer chains are at least 3 nm in length, further includes embodiments where the spacer chains are at least 3.5 nm in length, still further includes embodiments where the spacer chains are at least 4 nm in length and even further includes embodiments where the spacer chains are at least 5 nm in length.

The ability to extend and tailor the length of the spacer chains is particularly advantageous because longer spacer chains intercalated between a substrate surface and an immobilized bioactive molecule (e.g., an enzyme) can enhance significantly the activity of the immobilized biomolecule. In some instance, enzyme activities that are comparable to that of the free enzyme can be achieved by the extended spacer chains provided herein.

The first and second functional groups on the spacer molecules and the spacer chain extender molecules may be the same or different. The exact nature of these functional groups will depend on the functionalities present on the spacer molecules, spacer chain extender molecules, and any biomolecules to be immobilized on the surface. For example, when the spacer molecules and/or biomolecules are functionalized with primary amine groups, the spacer chain extender molecules should include functional groups, such as epoxy groups, that are reactive with primary amine groups. Suitable functional groups include, but are not limited to, amine groups, epoxy groups, aldehyde groups, hydroxyl groups, carboxy groups and mercapto groups. Examples of suitable spacer molecules include, but are not limited to, ethylene diamine and epichlorohydrin. Examples of suitable spacer chain extender molecules include, but are not limited to, dialdehyde molecules, such as glutaric dialdehyde, anhydride molecules, such as hexafluoroglutaric anhydride molecules, dichlorosilanes, such as dimethyldichlorosilane, epihalohydrins, such as epichlorohydrin and diepoxides, such as 1,4-butanediol diglycidyl ether. Molecules having chloracid groups may also be employed as spacer chain extender molecules. The chloracid groups on these molecules react readily with primary amine groups on spacer molecules and amine-containing biomolecules. However, it has been shown that the chloracid groups on such molecules are extremely reactive with atmospheric moisture and may be quickly deactivated before they have the opportunity to undergo reaction with amine-containing biomolecules, unless precautions are taken to avoid exposure of the chloracid groups to the atmosphere. See S. Alvarez-Blanco, et al., Polymer Bulletin, Vol. 47, 2001, pp. 329-336. Therefore, for many applications, less reactive terminal spacer molecule functionalities are recommended.

After the spacer chains or extended spacer chains are generated on the substrate surface, biomolecules may be immobilized on the surface by reacting the biomolecules with functionalities on the chains to form covalent bonds. This may be accomplished by venting the reactor chamber to bring it up to atmospheric pressure and exposing the spacer chains or extended spacer chains to selected biomolecules under conditions which promote covalent bond formation. Using this method, active biomolecules, such as enzymes, may be bound to a substrate while allowing freedom of movement and conformation comparable to that of the free molecule.

One important advantage realized by the plasma-enhanced surface treatments provided herein is that they are capable of providing a higher spacer chain density that wet chemical approaches. This, in turn, provides for a higher density of surface-bound biomolecules.

In some embodiments the biomolecules may be thiol-terminated or thiol-functionalized biomolecules or phosphate-terminated or phosphate-functionalized biomolecules and the spacer molecules or terminal spacer chain extender molecules include functional groups that react with thiol or phosphate groups to form covalent bonds. In other embodiments, the biomolecules are amine-containing or amine-functionalized biomolecules and the spacer molecules or terminal spacer chain extender molecules include functional groups that react with amine groups to form covalent bonds. The use of amine groups is advantageous because amine-based chemistries are less expensive to carry out and more stable than thiol-based chemistries.

Proteins are examples of biomolecules that may be usefully immobilized on the substrate surfaces. Other examples include oligonucleotides, aptamers, cDNA or RNA molecules. Still other examples include, but are not limited to, polypeptides, protein fragments, membrane proteins, antibodies, receptor fragments, antigens, enzymes and enzyme fragments.

The biomolecules may be immobilized on the spacer chains or extended spacer chains using conventional methods, including known wet chemical methods. Generally, this step entails contacting the surface-bound chains with an aqueous solution of a selected biomolecule (e.g., protein). For example, the surface may be suspended in an aqueous protein solution with optional incubation and stirring. As one of skill in the art will recognize, the reaction conditions (e.g., temperature, pH and exposure time) will depend on the particular system. Optionally, a chemical, such as a reducing agent, may be introduced after the substrates have been exposed to the biomolecules in order to strengthen the bonds between the biomolecules and the surface. The addition of a reducing agent leads to more stable covalent bonds when aldehyde-based attachment chemistries are used. Examples of suitable reducing agents include, but are not limited to sodium borohydride and sodium cyanoborohydride. Finally, the substrates may be rinsed with an appropriate solvent or buffer solution to remove unbound biomolecules.

The methods provided herein may be used to functionalize and attach biomolecules to a wide variety of carbon-containing substrates. One class of substrates that may be treated with the methods is polymeric substrates. These include polymeric substrates conventionally used to immobilize biomolecules, such as polycarbonate, polymethyl methacrylate and polystyrene substrates, including polystyrene microspheres. Polystyrene substrates are useful because they are inexpensive and may be processed to have a wide range of optical characteristics. Polycarbonate substrates are inexpensive, have high optical clarity and can have good impact strength. The methods may also be used to functionalize inert polymeric substrates, such as acetal, polyethylene, polypropylene, polyethylene terephthalate (PET) and polytetrafluoroethylene (PTFE) substrates, that cannot be functionalized efficiently with conventional wet chemistry approaches. These inert polymeric substrates may be functionalized in accordance with the present methods without pre-oxidation or irradiation. The polymeric substrates may be thin, flexible and/or transparent substrates.

Graphite substrates, diamond substrates and diamond-like carbon films may also be treated in accordance with the methods provided herein. Diamond and diamond-like carbon films provide tough abrasion-resistant surfaces with high melting temperatures that may be integrated into electronic systems. The diamond-like carbon films may be disposed on a variety of substrates, including polymeric substrates, metal substrates and ceramic substrates. Polymeric substrates on which the diamond-like carbon films may be disposed include, but are not limited to, poly(acrylic acid), poly(methyl methacrylate) and polycarbonate. Methods for producing diamond-like carbon films are known and include chemical vapor deposition using activated carbon-containing precursors (e.g., methane and acetylene), as well as thermal, plasma and combustion flame approaches. One suitable plasma-based technique for producing diamond-like carbon films ("hard-carbon films") on polymeric substrates is described in U.S. patent application Ser. No. 10/686,790, the entire disclosure of which is incorporated herein by reference. The diamond-like carbon films are characterized by high carbon contents and high hardness. For example, in some instances the carbon films have a carbon content of at least 80 atomic percent, desirably at least 85 atomic percent and more desirably at least 90 atomic percent. The films may have Mohs hardness values of at least 8 (measured by the wearing of a ruby ball dragged in a circular motion on the films during fretting wear tests), desirably at least 8.5 and more desirably at least 9.

Carbon nanotubes and nanoparticles are another class of substrate that may be treated with the methods provided herein. For the purposes of this disclosure, the term "nanotube" includes tubes of various lengths, including carbon filaments and carbon whiskers. Nanoparticles that may be treated with the methods provided herein include Buckyballs and quantum dots. Adducts of nanotubes or nanoparticles and biomolecules may be used in biosensing applications and as tools for implementing guided self-assembly of nanotubes and/or nanoparticles into ordered nanostructures. However, prior to the development of the present plasma treatment processes little progress had been made in developing methods for attaching biomolecules to carbon nanotubes or nanoparticles.

EXAMPLES

Materials and Methods: Unless otherwise specified, the following materials, equipment and methods were used in the examples below.

High purity argon and oxygen, employed to minimize the contamination of the reactor in the presence of plasma, were supplied by Liquid Carbonic. Ethylenediamine oxalyl chloride (OC), glutaric dialdehyde and epichlorohydrin, used for the surface functionalization reactions, were purchased from Aldrich Co. Fluorescamine was purchased from Molecular Probes Inc., (Eugene, Oreg.).

The DNA used in the experiments was composed of oligonucleotides 16 bases long with a C6-amino modifier on the 5' end and a fluorescein modifier on the 3' end. The base sequence of the oligonucleotides from the 5' end to the 3' end was as follows: amino-C6-CG AAC CTT CCT TAA GC-fluorescein. These oligonucleotides were synthesized by the University of Wisconsin Biotechnology Center using a commercial DNA synthesizer. The amine-containing oligonucleotides can be stored for extended periods of time (e.g., months or longer) in a freezer or refrigerator without degrading and require no lengthy purification steps before use. Deionized water was used to dilute the oligonucleotides to a usable concentration.

The argon plasma treatment of carbon-containing surfaces was carried out in a cylindrical stainless steel, capacitively coupled (disc-shaped stainless steel electrodes; electrode diameter: 20 cm; gap: 3 cm), RF-plasma-reactor, equipped with a 40 kHz power supply with pulsing capability, as shown in FIG. 1.

The measurements of attached oligonucleotides took place using a high resolution GeneTAC microarray fluorescence scanner (Genomics Solutions) normally used for analyzing standard glass slides. Fluorescence images were obtained after multiple washes of the treated surfaces and several days in a deionized water bath.

Example 1

Attachment of DNA to a Diamond-like Carbon Film

Polycarbonate slides were obtained from McMaster-Carr (Atlanta, Ga.). A diamond-like carbon film was formed on a polycarbonate slide according to the procedure described in U.S. patent application Ser. No. 10/686,790, the entire disclosure of which is incorporated herein by reference. Briefly, the polycarbonate slide was placed in a cylindrical, capacitively coupled, RF-plasma reactor made of stainless steel and equipped with a 40 kHz power supply. The plasma chamber was pumped down to a base pressure and an $SF_6$ plasma source gas was introduced into the chamber. A plasma of $SF_x$ (x<6) ion species was ignited in the chamber at about 200 Watts RF power and 200 mTorr pressure and sustained for at least about 5 minutes to provide a diamond-like carbon film on the surface of the substrate.

The diamond-like carbon film was then subjected to an argon plasma-treatment in the RF-plasma reactor under the following experimental conditions: Pressure of argon: 200 mTorr; RF-power dissipated to the electrodes: 200 W; Exposure time: 3 minutes. After the plasma treatment, the RF plasma chamber was pumped down to remove leftover reactive species.

Without breaking vacuum, a gas of ethylenediamine was introduced into the chamber and allowed to react with the plasma-treated surface. Covalent attachment of the ethylenediamine spacer molecules was performed by introducing the ethylenediamine vapors over the plasma-treated diamond-like carbon film under vacuum (pressure of ethylenediamine: 200-250 mTorr; reaction time: 30 minutes). The chamber was then pumped down again and the surfaces were exposed to a vapor of oxalyl chloride spacer molecules (pressure of oxalyl chloride: 200-250 mTorr; reaction time: 30 minutes). After this step, the remaining oxalyl chloride was vented and the chamber pressure brought up to atmosphere.

The surfaces were then ready for DNA deposition. The exposed chloracid groups on the spacer chains react readily with primary amine groups, allowing covalent attachment of amine-terminated DNA and proteins. However, the chloracid groups present on the surface were so reactive that they tended to react with atmospheric moisture. For this reason, the spacer-chain-capped surface was transferred to a vacuum desiccator as soon as the plasma chamber was brought up to atmosphere in order to avoid deactivation of the surface.

The deposition of the oligonucleotides onto the surface was done using an Eppendorf hand pipette capable of depositing 0.5 microliter spots. Immediately after removing the oligonucleotides from the desiccator, three spots of amine-terminated oligonucleotides and three spots of non-amine-terminated oligonucleotides were hand-pipetted onto each of the substrates. The surfaces were allowed to react in a dark, dry environment for 8 hours. During this period, the amine groups on the amine-modified oligonucleotides reacted with the chloracid functionalities present on the treated surfaces, where the unmodified oligonucleotides did not. They were then thoroughly washed to remove unbound oligonucleotides.

Figure 4:
FIG. 4 shows a fluorescence image of fluorescently-tagged oligonucleotides immobilized on a diamond-like carbon film.

Results:

The measurement of attached oligonucleotides took place using a low-resolution FluorImager fluorescence scanner (Molecular Dynamics) normally used for analyzing electrophoresis gels. Fluorescence images were obtained after multiple washes of the treated surface and several days in a deionized water bath, to remove all non-covalently bound oligonucleotides. A scan of the treated diamond-like carbon film is presented in FIG. 4. In the figure, the fluorescent spots (box) corresponding to immobilized amine-terminated oligonucleotides are clearly visible while spots corresponding to the non-amine-terminated oligonucleotides are absent.

Example 2

Attachment of DNA to a Polycarbonate Substrate

A polycarbonate slide, obtained from McMaster-Carr (Atlanta, Ga.), was subjected to a plasma treatment in the RF-plasma reactor under the following experimental conditions: Pressure of argon: 200 mTorr; RF-power dissipated to the electrodes: 200 W; Exposure time: 3 minutes. After the plasma treatment, the RF plasma chamber was pumped down to remove leftover reactive species.

Without breaking vacuum, a gas of ethylenediamine was introduced into the chamber and allowed to react with the plasma-treated surface. Covalent attachment of the ethylenediamine spacer molecules was performed by introducing the ethylenediamine vapors over the plasma-treated polycarbonate surface under vacuum (pressure of ethylenediamine: 200-250 mTorr; reaction time: 30 minutes). The chamber was then pumped down again and the surfaces were exposed to a vapor of glutaric dialdehyde spacer molecules (pressure of glutaric dialdehyde: 200-250 mTorr; reaction time: 30 minutes). After this step, the remaining glutaric dialdehyde was vented and the chamber pressure brought up to atmosphere.

The surfaces were then ready for DNA deposition. The exposed aldehyde groups on the spacer chains do not react with or become deactivated by atmospheric moisture. Therefore, the spacer-chain-capped surface did not need to be transferred to a vacuum desiccator.

The deposition of the oligonucleotides onto the surface was done using an Eppendorf hand pipette capable of depositing 0.5 microliter spots. The polycarbonate slides were spotted in three places using amine-terminated oligonucleotides and in three places using fluorescently-tagged, but not amine-terminated, oligonucleotides. The surface was allowed to react in a dark, dry environment for 8 hours. To reduce the aldehyde-amine bonds and make them more stable, a solution of 4 mg sodium borohydride in 200 proof ethanol was spread over the sample surface and allowed to react for 30 minutes. The surface was then washed to remove unbound oligonucleotides.

Figure 5:
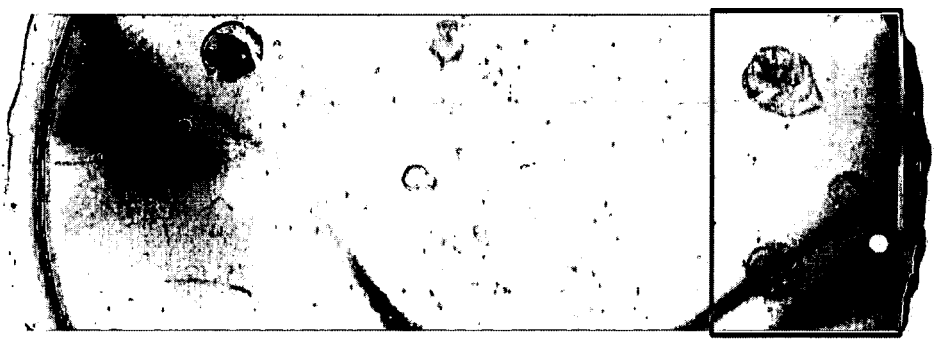
FIG. 5 shows a fluorescence image of fluorescently-tagged oligonucleotides immobilized on a polycarbonate substrate.

Results:

A scan of the treated polycarbonate surface is presented below in FIG. 5. In the figure, the three fluorescent spots corresponding to immobilized amine-terminated oligonucleotides (box) are clearly visible while spots corresponding to the non-amine-terminated oligonucleotides are absent.

Example 3

Attachment of DNA to Carbon Nanotubes

A suspension of single-walled carbon nanotubes in toluene was obtained from Carbon Nanotechnologies, Inc. Drops of a carbon nanotube-containing solution, were placed on two standard glass slides. One drop was placed at each corner of the two glass slides.

The carbon nanotubes were subjected to an argon plasma-treatment in the RF-plasma reactor under the following experimental conditions: Pressure of argon: 200 mTorr; RF-power dissipated to the electrodes: 200 W; Exposure time: 3 minutes. After the plasma treatment, the RF plasma chamber was pumped down to remove leftover reactive species.

Without breaking vacuum, a gas of ethylenediamine was introduced into the chamber and allowed to react with the plasma-treated nanotubes. Covalent attachment of the ethylenediamine spacer molecules was performed by introducing the ethylenediamine vapors over the plasma-treated nanotubes under vacuum (pressure of ethylenediamine: 200-250 mTorr; reaction time: 30 minutes). The chamber was then pumped down again and the nanotubes were exposed to a vapor of glutaric dialdehyde spacer molecules (pressure of glutaric dialdehyde: 200-250 mTorr; reaction time: 30 minutes). After this step, the remaining glutaric dialdehyde was vented and the chamber pressure brought up to atmosphere. The second slide did not undergo plasma treatment or gas phase functionalization.

Both slides were then exposed to the amine-terminated, fluorescently tagged oligonucleotides. The deposition of the oligonucleotides onto the slides was done using an Eppendorf hand pipette which deposited a 0.5 microliter spot in each corner of both slides, over the nanotube "spots". The slides were allowed to react in a dark, dry environment for 8 hours. The slides were then washed to remove unbound oligonucleotides.

Figure 6:
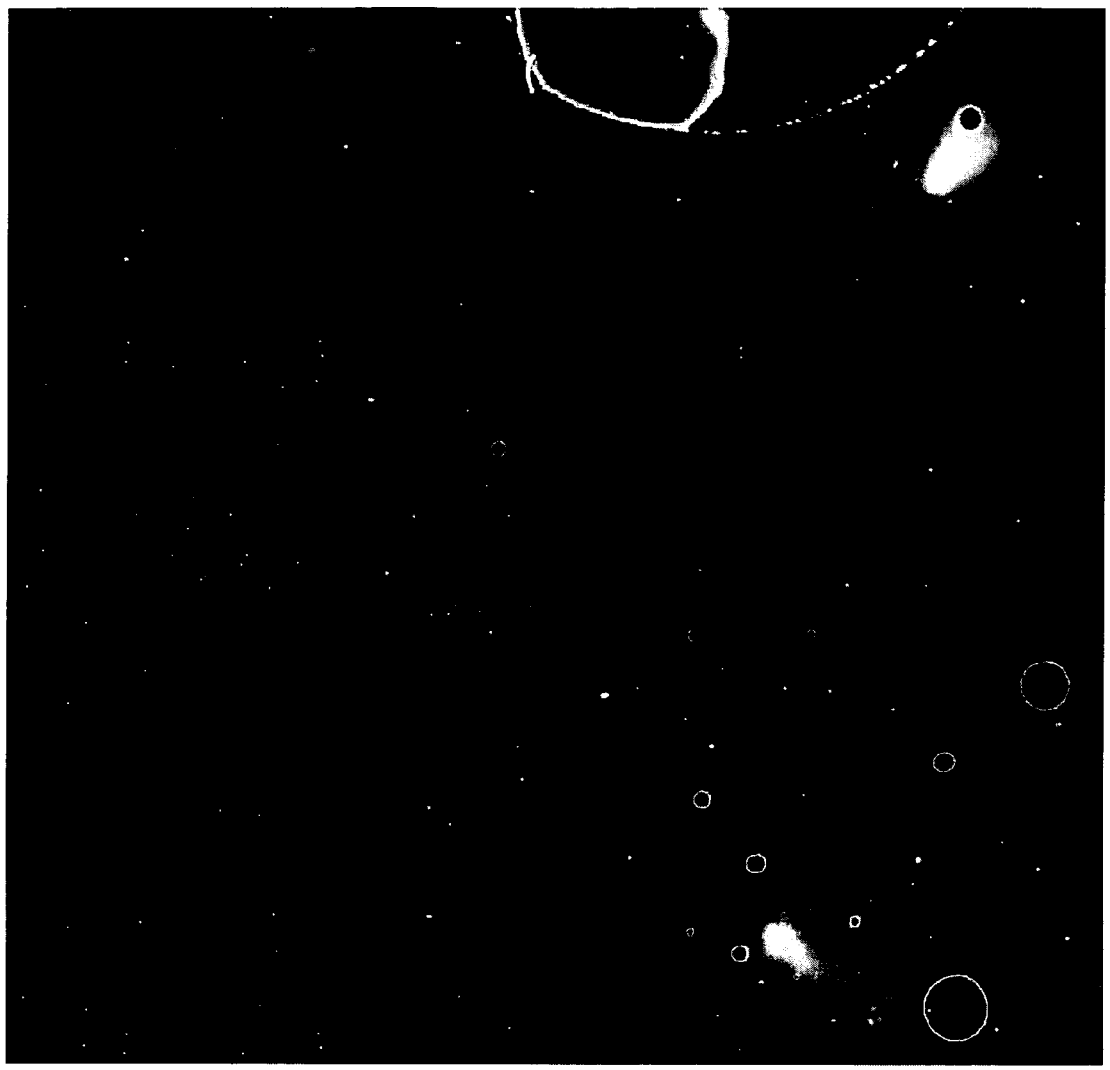
FIG. 6 shows a fluorescence image of fluorescently-tagged oligonucleotides immobilized on carbon nanotubes.
Figure 7:
FIG. 7 shows a fluorescence image of a non-plasma treated, non-functionalized control sample of carbon nanotubes.

Results:

FIG. 6 shows the fluorescence image of the amine-terminated oligonucleotides on the plasma-treated slide. As seen in the figure, fluorescent spots appear in three corners (upper left, upper right and lower right) of the slide. The absence of a fluorescent spot in the lower left corner is likely due to experimental error in depositing the nanotubes on the slide. FIG. 7 shows the fluorescence image of the non-plasma-treated control slide. As shown in the image, no fluorescent spots are visible at the corners of the slide.

Example 4

Attachment of DNA to a Delrin® Substrate

This example describes a system wherein a carbon-containing surface is functionalized with a molecule capable of forming a first covalent bond to a carbon-containing surface and a second covalent bond to a biomolecule.

Delrin® (an acetal plastic) sheets were obtained from McMaster-Carr (Atlanta, Ga.) and were cut into slide-sized pieces. A slide was then subjected to an argon plasma-treatment in the RF-plasma reactor under the following experimental conditions: Pressure of argon: 200 mTorr; RF-power dissipated to the electrodes: 200 W; Exposure time: 3 minutes. After the plasma treatment, the RF plasma chamber was pumped down to remove leftover reactive species.

Without breaking vacuum, covalent attachment of the epichlorohydrin molecules was performed by introducing the epichlorohydrin vapors over the plasma-treated surface under vacuum (pressure of epichlorohydrin: 200-250 mTorr; reaction time: 30 minutes). After this step, the remaining epichlorohydrin was vented and the chamber pressure brought up to atmosphere.

The deposition of the oligonucleotides onto the surface was done using the fluid dispensation apparatus described in Rev. Sci. Instru., 75, 832 (2004) and in U.S. patent application Ser. No. 10/271,250, the entire disclosures of which are incorporated herein by reference. Briefly, a glass capillary having an interior diameter of approximately 1-100 micron and a piezoelectric actuator coupled to a portion of its circumference was dipped into a 200 µM solution of the above-described DNA molecules in water and a quantity of the solution was pulled into the capillary by capillary action. The Delrin® substrate was disposed below the capillary on a substrate mount. Controlled by a positioning stage, the capillary was placed in contact with the substrate. The piezoelectric actuator was then activated at a frequency of 660 kHz with a voltage of 1 volt (peak-to-peak) for about 250 milliseconds to deposit a spot of solution from the capillary onto the surface of the substrate. The capillary was then moved relative to the substrate mount and the process was repeated to provide two triangular patterns and a pattern in the shape of the word "plasma". The samples were allowed to react in a dark, dry environment for 2 hours. They were then washed to remove unbound oligonucleotides.

Figure 8:
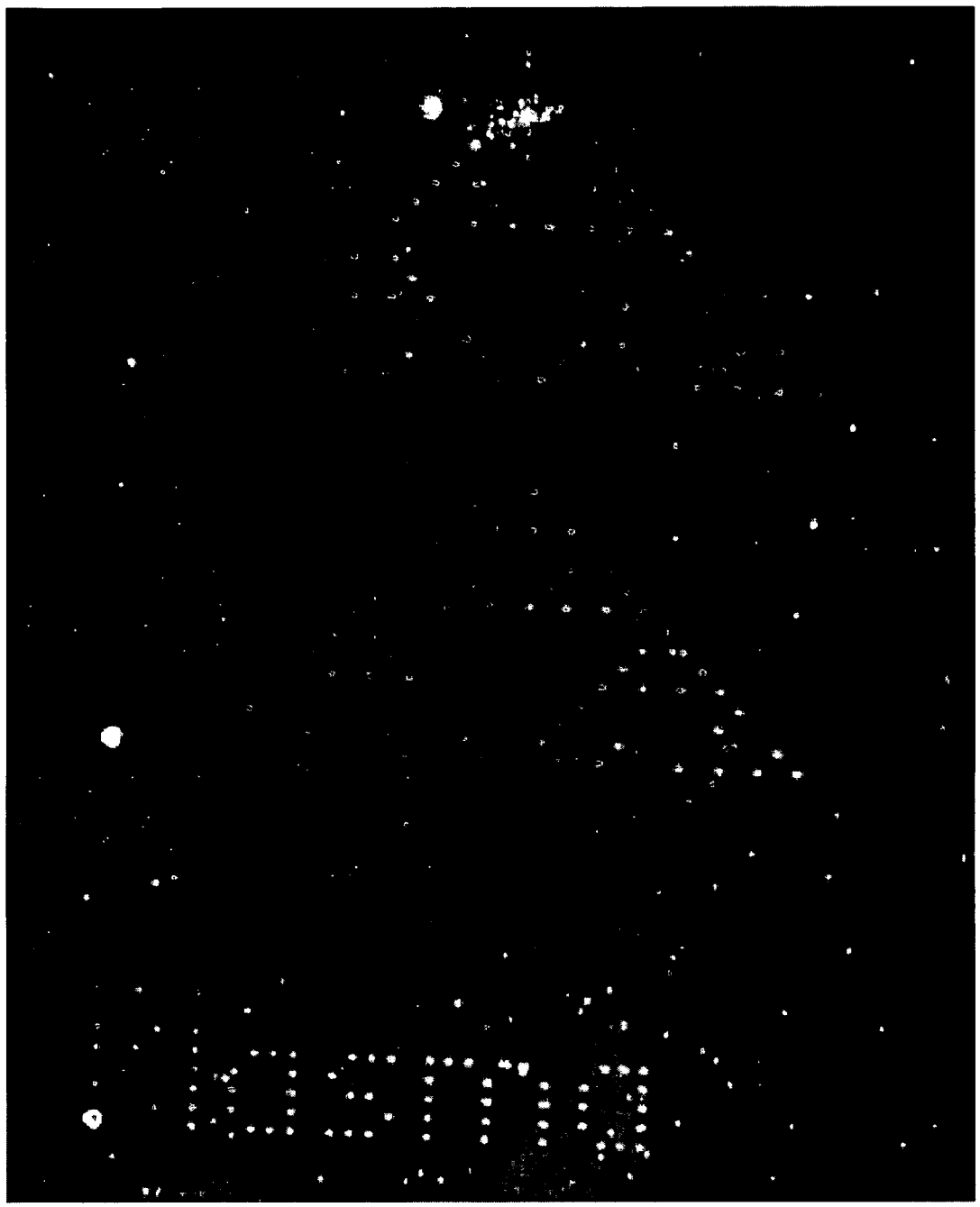
FIG. 8 shows a fluorescence image of fluorescently-tagged oligonucleotides immobilized on a Delrin® slide.

Results:

A scan of the treated Delrin® slide is presented below in FIG. 8. In the figure, patterns of fluorescent spots in the shape of two triangular patterns and the word "plasma" corresponding to immobilized amine-terminated oligonucleotides are clearly visible.

Example 5

Attachment of DNA to a Delrin® Substrate with an Extended Spacer Chain

This example describes the formation of an extended spacer chain through sequential gas phase chain extension reactions.

Delrin® (an acetal plastic) sheets were obtained from McMaster-Carr (Atlanta, Ga.) and were cut into slide-sized pieces. A slide is subjected to an argon plasma treatment in the RF plasma reactor under the following experimental conditions: Pressure of argon: 200 mTorr; RF-power dissipated to the electrodes: 200 W; Exposure time: 3 minutes. After the plasma treatment, the RF plasma chamber is pumped down to remove leftover reactive species.

Without breaking vacuum, covalent attachment of the epichlorohydrin molecules is performed by introducing epichlorohydrin vapors over the plasma-treated surface under vacuum (pressure of epichlorohydrin: 200-250 mTorr; reaction time: 30 minutes). After this step, the chamber is pumped down to remove any remaining epichlorohydrin. Next, without breaking vacuum, ethylenediamine vapors are introduced into the chamber (pressure of ethylenediamine: 200-250 mTorr; reaction time: 30 minutes). The chamber is then pumped down again. This two-step procedure is repeated one more time by reintroducing epichlorohydrin vapors into the chamber, pumping down the chamber, then reintroducing ethylenediamine into the chamber, and pumping down once more. Finally, the spacer chain may be terminated by introducing epichlorohydrin vapors into the chamber one final time. The remaining epichlorohydrin is then vented and the chamber pressure is brought up to atmosphere. The resulting spacer chain is at least 2.5 nm in length. Alternatively, the spacer chains may be extended further by repeating the two step procedure one (or more) additional times before terminating the chains with epichlorohydrin. The resulting spacer chains are at least 5 nm in length.

The deposition of the oligonucleotides onto the surface is done using the fluid dispensation apparatus described in U.S. patent application Ser. No. 10/271,250, as discussed in Example 4.

It is understood that the invention is not limited to the embodiments set forth herein for illustration, but embraces all such forms thereof as come within the scope of the following claims:

What is claimed is:

1. A surface treated polymer comprising:
   (a) a polymer surface, wherein the polymer is selected from the group consisting of an acetal plastic, polyethylene, polypropylene, polyethylene terephthalate, and polytetrafluoroethylene;
   (b) spacer chains covalently bound to the polymer surface, the spacer chains formed by reacting molecules selected from the group consisting of epichlorohydrin, epibromohydrin, epifluorohydrin, and combinations thereof with the polymer surface; and
   (c) biomolecules covalently bound to the spacer chains.

2. The polymer of claim 1, wherein the one or more spacer chains have a length of at least 2.5 nm.

3. The polymer of claim 1, wherein the one or more spacer chains have a length of at least 4 nm.

4. The polymer of claim 1, wherein the one or more spacer chains have a length of at least 5 nm.

5. The polymer of claim 1, wherein the one or more biomolecules are proteins.

6. The polymer of claim 1, wherein the one or more biomolecules are enzymes.

7. The polymer of claim 1, wherein the one or more biomolecules are oligonucleotides.

8. A surface treated carbon-containing nanotube or nanoparticle comprising:
   (a) a carbon-containing nanotube or nanoparticle;
   (b) spacer chains covalently bound to the nanotube or nanoparticle; and
   (c) biomolecules covalently bound to the spacer chains;
   wherein the spacer chains are formed from molecules selected from the group consisting of dialdehyde molecules, anhydride molecules, dichloride molecules, epihalohydrin molecules, diepoxide molecules and combinations thereof.

9. The surface treated carbon-containing a nanotube or nanoparticle of claim 8, wherein the spacer chains have a length of at least 2.5 nm.

10. The carbon-containing nanotube or nanoparticle of claim 8, wherein the spacer chains are bound to the nanotube or nanoparticle by reacting molecules selected from the group consisting of epichlorohydrin, epibromohydrin, epifluorohydrin, 1,4-butanediol diglycidyl ether and combinations thereof with the nanotube or nanoparticle.

11. A surface treated diamond-like carbon film comprising:
   (a) a diamond-like carbon film;
   (b) spacer chains covalently bound to the diamond-like carbon film; and
   (c) biomolecules covalently bound to the spacer chains;

wherein the spacer chains are formed from molecules selected from the group consisting of dialdehyde molecules, anhydride molecules, dichloride molecules, epihalohydrin molecules, diepoxide molecules and combinations thereof.

12. The diamond-like carbon film of claim 11, wherein the diamond-like carbon film is disposed on a substrate.

13. The surface-treated diamond-like carbon film of claim 11, wherein the spacer chains have a length of at least 2.5 nm.

14. The diamond-like carbon film of claim 11, wherein the spacer chains are bound to the diamond-like carbon film by reacting molecules selected from the group consisting of epichlorohydrin, epibromohydrin, epifluorohydrin, 1,4-butanediol diglycidyl ether and combinations thereof with the diamond-like carbon film.

* * * * *